US009380995B2

(12) United States Patent
Lee et al.

(10) Patent No.: US 9,380,995 B2
(45) Date of Patent: Jul. 5, 2016

(54) ULTRASOUND SYSTEM FOR MEASURING IMAGE USING FIGURE TEMPLATE AND METHOD FOR OPERATING ULTRASOUND SYSTEM

(75) Inventors: Kwang-Hee Lee, Daejeon (KR); Sung Yoon Kim, Namyangju-si (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 55 days.

(21) Appl. No.: 13/092,372

(22) Filed: Apr. 22, 2011

(65) Prior Publication Data
US 2011/0282199 A1 Nov. 17, 2011

(30) Foreign Application Priority Data

May 17, 2010 (KR) .................... 10-2010-0046042
May 17, 2010 (KR) .................... 10-2010-0046043
May 17, 2010 (KR) .................... 10-2010-0046044

(51) Int. Cl.
*A61B 8/08* (2006.01)
*A61B 5/107* (2006.01)
*A61B 8/00* (2006.01)

(52) U.S. Cl.
CPC ............ *A61B 8/0866* (2013.01); *A61B 5/1075* (2013.01); *A61B 8/463* (2013.01); *A61B 8/469* (2013.01); *A61B 8/0858* (2013.01)

(58) Field of Classification Search
CPC .................................................. A61B 8/0866
USPC .................................. 600/407, 437
See application file for complete search history.

(56) References Cited

U.S. PATENT DOCUMENTS

| 5,795,296 | A | 8/1998 | Pathak et al. |
| 5,838,592 | A | 11/1998 | Spratt |
| 7,738,683 | B2 * | 6/2010 | Cahill et al. .................. 382/128 |
| 8,204,288 | B2 | 6/2012 | Kim et al. |
| 2006/0122489 | A1 * | 6/2006 | Kato et al. .................... 600/411 |
| 2007/0006651 | A1 | 1/2007 | Kruger et al. |
| 2008/0188748 | A1 * | 8/2008 | Sonek et al. .................. 600/443 |
| 2009/0052756 | A1 * | 2/2009 | Saddi et al. .................... 382/131 |
| 2009/0228813 | A1 | 9/2009 | Sekiguchi |

(Continued)

FOREIGN PATENT DOCUMENTS

| EP | 2387949 A1 | 11/2011 |
| JP | 7-116159 A | 5/1995 |
| JP | 2009-207872 | 9/2009 |

(Continued)

OTHER PUBLICATIONS

Korean Office Action issued in Application No. 10-2010-0046043 issued on Mar. 20, 2012.

(Continued)

*Primary Examiner* — Rochelle Turchen
(74) *Attorney, Agent, or Firm* — McDermott Will & Emery LLP (57) ABSTRACT

Provided are a three-dimensional (3D) ultrasound system and a method for operating the 3D ultrasound system. The 3D ultrasound system may include a display unit to form an image with respect to an object in the body and to display the image on a screen, and a control unit to generate a figure template corresponding to the image, to adjust the generated figure template based on a reference location of the image, and to superimpose the adjusted figure template on the image and display the resulting combination.

11 Claims, 10 Drawing Sheets

(56) References Cited

U.S. PATENT DOCUMENTS

2010/0125202 A1 5/2010 Lee et al.
2011/0282199 A1 11/2011 Lee et al.

FOREIGN PATENT DOCUMENTS

| | | |
|---|---|---|
| JP | 2010-000305 | 1/2010 |
| KR | 10-2008-0031004 A | 4/2008 |
| KR | 2008-0095229 A | 10/2008 |
| KR | 10-2010-0056253 A | 5/2010 |
| WO | WO 2005/015499 A2 | 2/2005 |
| WO | WO 2008/072157 A2 | 6/2008 |
| WO | WO 2009/136332 A2 | 11/2009 |

OTHER PUBLICATIONS

Extended European Search Report issued in European Patent Application No. EP 11163076.0 dated Sep. 15, 2011.
S. Nirmala et al., "Clinical decision support system for early prediction of Down syndrome fetus using sonogram images," Signal, Image and Video Processing, Springer-Verlag, London, vol. 5, No. 2, Mar. 12, 2010, XP019901526.
Korean Office Action issued in Korean Patent Application No. 10-2010-0046042 dated Dec. 27, 2011.
Korean Office Action issued in Korean Patent Application No. 10-2010-0046044 dated Dec. 27, 2011.
Office Action dated Oct. 29, 2012 of Korean Patent Application No. 10-2010-0046043.
Korean Final Office Action issued in Korean Application No. 10-2010-0046043 dated May 30, 2013 with English Translation.
Korean Final Office Action issued in Korean Application No. 10-2010-0046043 dated Aug. 19, 2013 with English Translation.
Korean Notice of Allowance issued in Korean Application No. 10-2010-0046043 dated Jan. 7, 2015, with English Translation.
Japanese Non-Final Rejection issued in Japanese Application No. 2011-101857 dated Jan. 27, 2015, with English Translation.
Japanese Notice of Allowance issued in Japanese Application No. 2011-101857 issued Oct. 20, 2015, with English Translation.

* cited by examiner

ULTRASOUND SYSTEM FOR MEASURING IMAGE USING FIGURE TEMPLATE AND METHOD FOR OPERATING ULTRASOUND SYSTEM

CROSS-REFERENCE TO RELATED APPLICATIONS

This application claims the benefit of Korean Patent Application No. 10-2010-0046042, filed on May 17, 2010, Korean Patent Application No. 10-2010-0046043, filed on May 17, 2010, and Korean Patent Application No. 10-2010-0046044, filed on May 17, 2010, in the Korean Intellectual Property Office, the disclosures of which are incorporated herein by reference.

BACKGROUND

1. Field of the Invention

The present invention relates to a three-dimensional (3D) ultrasound system which may automatically measure an image of an object in the body by adjusting a figure template corresponding to the image, and a method for operating the 3D ultrasound system.

2. Description of the Related Art

An ultrasound system is an apparatus for transmitting, from the surface of the body, an ultrasound wave signal toward a predetermined structure, that is, an object such as a fetus or an internal organ, inside the body, and for visualizing a cross section of soft tissues or a blood flow using information of the ultrasound wave signal reflected from the tissues of the body. This ultrasound system has advantages of a small size, a low cost, a real-time display, and a high stability without exposing patients and users to x-ray radiation, and thus, the ultrasound system is widely used along with other diagnostic imaging systems such as an x-ray diagnosis equipment, a computerized tomography (CT) scanner, a magnetic resonance imaging (MRI) equipment, a nuclear medicine diagnosis equipment, and the like.

When the ultrasound system measures an object in the body, the ultrasound system forms an image of the object by irradiating the object with an ultrasonic beam, superimposes a figure template corresponding to the image on the image, and displays the resulting combination. In this instance, the ultrasound system may adjust and display the figure template using a combination of a trackball and a set button controlled by a user. It is inevitable to measure the object using the ultrasound system without intervention of the user, which may make accurate measurement impossible.

Accordingly, there is a desire for an ultrasound system for easily providing an accurate measurement result with a minimum intervention of a user by automation of a series of object measuring processes.

SUMMARY

An aspect of the present invention provides a three-dimensional (3D) ultrasound system and a method for operating the 3D ultrasound system, which may generate a figure template corresponding to an image, may adjust the generated figure template to be matched with the image by rotating, moving, or modifying the figure template based on a reference location of the image, and may display feature information of the matched figure template, for example, biparietal diameter (BPD), occipitofrontal diameter (OFD), head circumference (HD), or a ratio of BPD/OFD, thereby automatically providing an accurate measurement result of the image.

According to an aspect of the present invention, there is provided a 3D ultrasound system including a display unit to form an image with respect to an object in the body and to display the image on a screen, and a control unit to generate a figure template corresponding to the image, to adjust the generated figure template based on a reference location of the image, and to superimpose the adjusted figure template on the image and display the resulting combination.

According to another aspect of the present invention, there is provided a method for operating a 3D ultrasound system including forming an image with respect to an object in the body and displaying the image on a screen, generating a figure template corresponding to the image and adjusting the generated figure template based on a reference location of the image, and superimposing the adjusted figure template on the image and displaying the resulting combination.

Effect of the Invention

According to an aspect of the present invention, provided are a three-dimensional (3D) ultrasound system and a method for operating the 3D ultrasound system, which may generate a figure template corresponding to an image, may adjust the generated figure template to be matched with the image by rotating, moving, or modifying the figure template based on a reference location of the image, and may display feature information of the matched figure template, for example, biparietal diameter (BPD), occipitofrontal diameter (OFD), head circumference (HD), or a ratio of BPD/OFD, thereby automatically providing an accurate measurement result of the image.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which.

DETAILED DESCRIPTION

Reference will now be made in detail to exemplary embodiments of the present invention, examples of which are illustrated in the accompanying drawings, wherein like reference numerals refer to the like elements throughout. Exemplary embodiments are described below to explain the present invention by referring to the figures.

Figure 1:
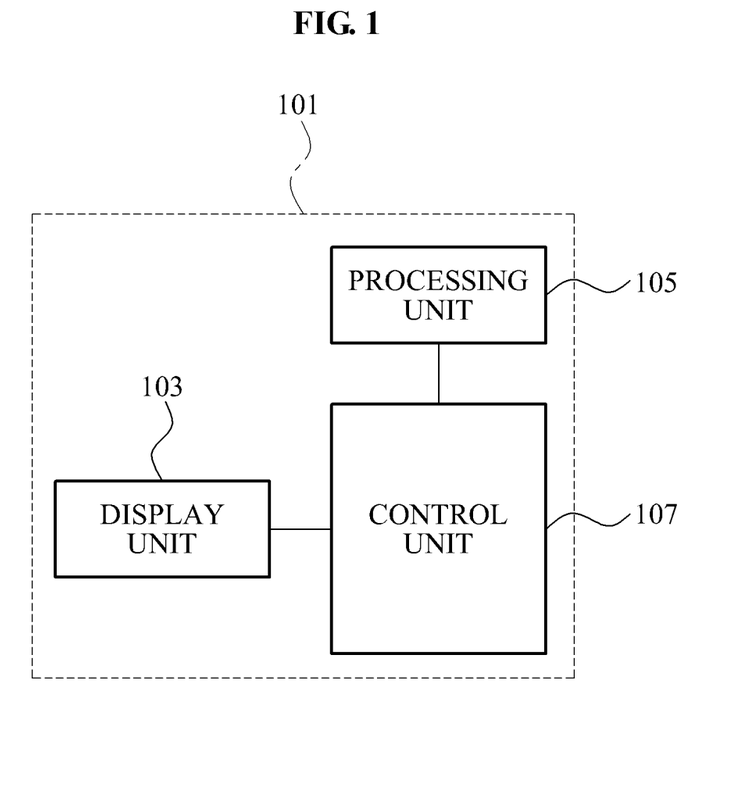
FIG. 1 is a block diagram illustrating a structure of a three-dimensional (3D) ultrasound system according to an embodiment of the present invention.

FIG. 1 is a block diagram illustrating a structure of a three-dimensional (3D) ultrasound system 101 according to an embodiment of the present invention.

Referring to FIG. 1, the 3D ultrasound system 101 according to an embodiment of the present invention may include a display unit 103, a processing unit 105, and a control unit 107.

The display unit 103 may form an image with respect to an object in the body, and may display the image on a screen. Here, the object in the body may be a fetus, a blood vessel, or an internal organ.

For example, the display unit 103 may set a region of interest (ROI), that is, an ROI in the object, may locate a seed within the set ROI, and may form an image of the object by irradiating the object with an ultrasonic beam.

The processing unit 105 may perform a thresholding operation on the image based on predetermined brightness information. For example, the processing unit 105 may make the contour of the image clear by turning the image 'black' or 'white' depending on '0' and '1' given based on predetermined brightness information.

Also, the processing unit 105 may clearly distinguish an area to be measured in the image, by performing an edge detecting operation or an ellipse fitting operation on the image.

The control unit 107 may generate a figure template corresponding to the image, for example, a circular or ellipse template, may adjust the generated figure template based on a reference location of the image, for example, a central point of the image, and may superimpose the adjusted figure template on the image and display the resulting combination.

In this instance, the control unit 107 may adjust the generated figure template based on location information inputted by an interface unit (not shown), for example, a point resulted from focusing on the image, or based on a central point of the object measured by a center extracting unit (not shown), as the reference location. Here, when the object is a fetus, the center extracting unit may generate a central point of the object using a first specific point related to the ridge of the nose of the fetus and a second specific point related to the jawbone of the fetus, and may provide the control unit 107 with the generated central point of the object as the reference location.

The control unit 107 may adjust the generated figure template by rotating, moving, or modifying the figure template based on the reference location of the image, and the modification may change the biparietal diameter (BPD) or the occipitofrontal diameter (OFD) of the figure template. For example, the control unit 107 may finely adjust the generated figure template to be matched with the image, by changing an angle of the figure template through rotation of the figure template, by changing a location of the figure template through movement of the figure template, or by changing a size of the figure template through a change in BPD or OFD of the figure template.

In this instance, the control unit 107 may adjust the generated figure template with a minimum matching energy with the image. That is, the control unit 107 may adjust the generated figure template to be matched with the image at the maximum while reducing the matching energy by minimizing rotation, movement, or modification of the figure template.

When adjustment of the figure template is completed by the control unit 107, the display unit 103 may display at least one of BPD, OFD, head circumference (HD), and a ratio of BPD/OFD of the adjusted figure template. For example, when the object is a fetus, the display unit 103 may display at least one of BPD, OFD, HD, and a ratio of BPD/OFD of the adjusted ellipse template. Accordingly, an operator or a doctor may accurately and easily diagnose a feature of a fetus to be measured.

Figure 2:
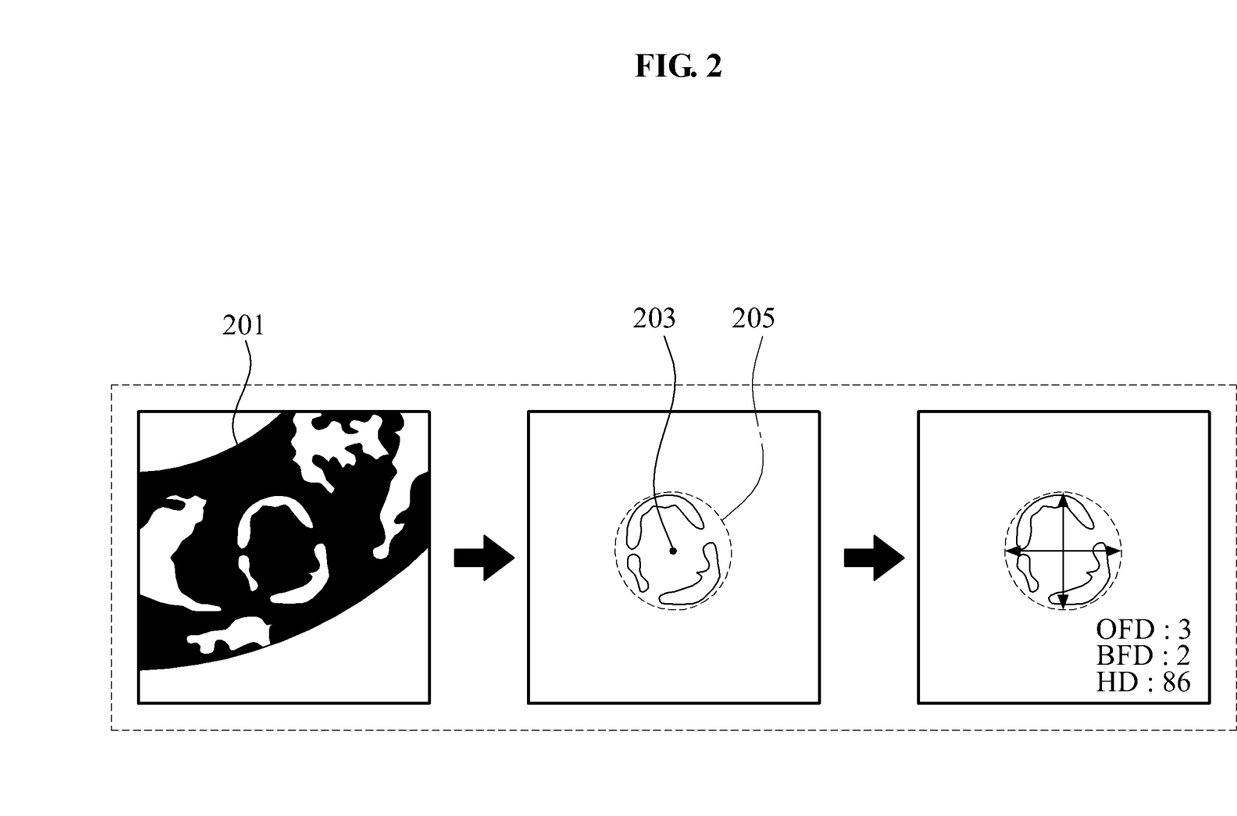
FIG. 2 is a view illustrating an example of an image of an object displayed while being measured by the 3D ultrasound system according to an embodiment of the present invention.

FIG. 2 is a view illustrating an example of an image of an object displayed while being measured by the 3D ultrasound system according to an embodiment of the present invention.

Referring to FIG. 2, the 3D ultrasound system may form an image with respect to an object in the body and may display the image on a screen. For example, the 3D ultrasound system may form an image with respect to the head of a fetus, and may display the image 201, for example, an image viewed down from the head. In this instance, the 3D ultrasound system may clearly distinguish an area to be measured, by performing a thresholding operation, an edge detecting operation, or an ellipse fitting operation.

The 3D ultrasound system may generate a figure template corresponding to the image, may adjust the generated figure template based on a reference location of the image, and may superimpose the adjusted figure template on the image and display the resulting combination. For example, the 3D ultrasound system may generate an ellipse template 205 corresponding to the fetal head image, may adjust the generated ellipse template based on a central point 203 of the fetal head image, and may superimpose the adjusted ellipse template 205 on the fetal head image and display the resulting combination.

The 3D ultrasound system may display feature information of the adjusted figure template. For example, the 3D ultrasound system may display at least one of BPD, OFD, HD, and a ratio of BPD/OFD of the adjusted ellipse template corresponding to the fetal head image.

Figure 3:
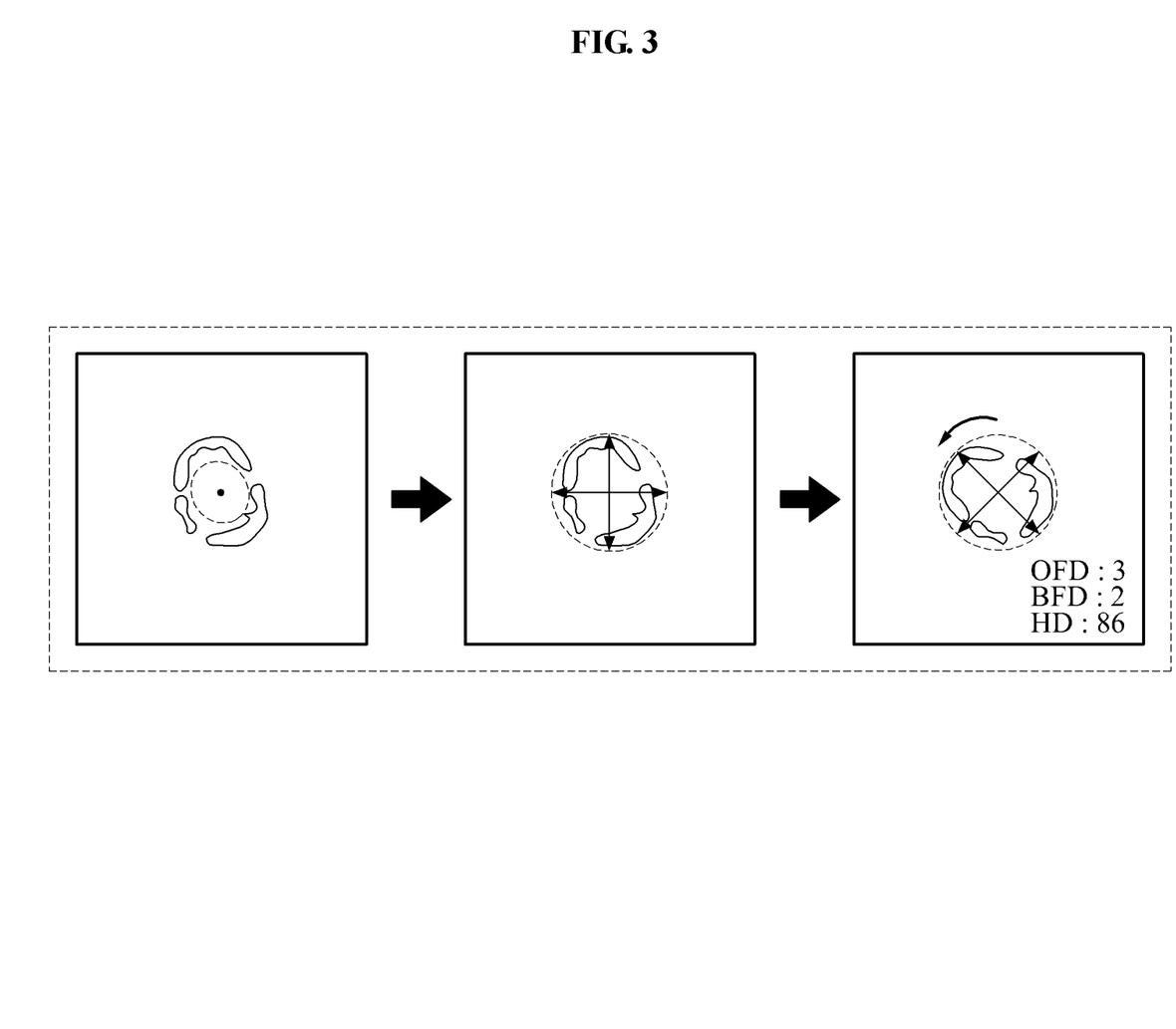
FIG. 3 is a view illustrating an example of adjustment of a figure template in the 3D ultrasound system according to an embodiment of the present invention.

FIG. 3 is a view illustrating an example of adjustment of a figure template in the 3D ultrasound system according to an embodiment of the present invention.

Referring to FIG. 3, the 3D ultrasound system may form an image with respect to an object in the body, and may display the image and a figure template corresponding to the image on a screen. In this instance, the 3D ultrasound system may rotate, move, or modify the figure template based on a reference location of the image.

For example, the 3D ultrasound system may display the ellipse template corresponding to the fetal head image, and may match the ellipse template with the fetal head image by modifying the BPD or OFD of the ellipse template in a lengthwise direction. Also, when an angular adjustment of the ellipse template is needed, the 3D ultrasound system may rotate the ellipse template to be matched with the fetal head image more accurately.

Figure 4:
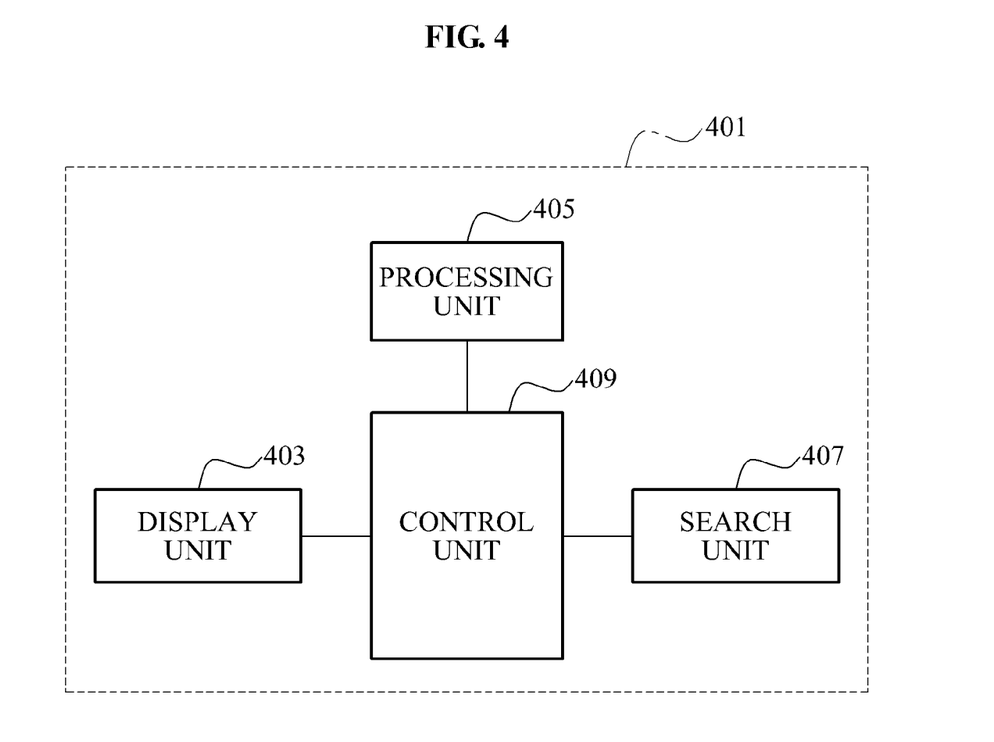
FIG. 4 is a block diagram illustrating a structure of a 3D ultrasound system according to another embodiment of the present invention.

FIG. 4 is a block diagram illustrating a structure of a 3D ultrasound system 401 according to another embodiment of the present invention.

Referring to FIG. 4, the 3D ultrasound system 401 according to another embodiment of the present invention may include a display unit 403, a processing unit 405, a search unit 407, and a control unit 409.

The display unit 403 may form an image with respect to an object in the body, and may display the image on a screen. Here, the object in the body may be a fetus, a blood vessel, or an internal organ.

In this instance, the display unit 403 may extract, from the image of the object, an image based on an inputted seed, for example, a surrounding image relative to the seed, and may display the extracted image. Here, when the object is a fetus, the seed may be located near the nuchal translucency (NT) of the fetus.

Also, the display unit 403 may extract a partial image from the image with respect to the entire object, however the present invention is not limited in this regard. The display unit 403 may obtain an image with respect to a portion of the object. That is, the display unit 403 may set an ROI in the object, may locate a seed within the set ROI, and may form an image of a portion of the object.

The processing unit 405 may perform a thresholding operation or a multiplying operation on the extracted image based on predetermined brightness information. For example, the processing unit 405 may make the contour of the extracted image clear by turning the image 'black' or 'white' depending on '0' and '1' given based on predetermined brightness information through a thresholding operation. Also, the processing unit 405 may make a bright area brighter and a dark area darker through a multiplying operation, thereby facilitating a search for a gradient peak of the extracted image.

The search unit 407 may search for a zero-crossing based on the seed, and may search for a gradient peak of the extracted image using the found zero-crossing. Specifically, the search unit 407 may search for a first zero-crossing in an upper area and a second zero-crossing in a lower area based on the seed, and may search for a first gradient peak and a second gradient peak of the extracted image using the first zero-crossing and the second zero-crossing, respectively.

In this instance, the search unit 407 may locate a plurality of seeds on a horizontal line including the seeds, and may search for a gradient peak using each of the seeds. Here, the search unit 407 may search for a first gradient peak and a second gradient peak of different locations for each of the plurality of seeds.

The control unit 409 may measure a thickness of the extracted image using the found gradient peak. In this instance, the control unit 409 may measure a distance between the first gradient peak and the second gradient peak searched by the search unit 407.

For example, when the extracted image is the NT of a fetus, the control unit 409 may search for a first gradient peak and a second gradient peak along the boundary of a transparent space located at the back of the neck of the fetus, and may measure a distance between the found first gradient peak and the found second gradient peak, so that a thickness of the NT of the fetus may be easily measured. Accordingly, an operator or a doctor may accurately and easily diagnose abnormalities of the fetus based on the measured NT thickness.

Also, when the first gradient peak and the second gradient peak for each of the plurality of seeds are found, the control unit 409 may measure a distance between the first gradient peak and the second gradient peak, respectively. Subsequently, the control unit 409 may determine one of a plurality of distances, that is, one of a plurality of thicknesses of the image, and may display the determined one on the display unit 403, thereby providing a more accurate thickness of the image.

For example, the control unit 409 may calculate an average and a variation of the measured thicknesses of the image, and may determine a maximum thickness among thicknesses of the image smaller than the sum of the average and the variation. Subsequently, the control unit 409 may superimpose the determined thickness or a gradient peak corresponding to the determined thickness on the extracted image, and may display the resulting combination, thereby facilitating recognition of an area where the thickness of the image was measured.

Figure 5:
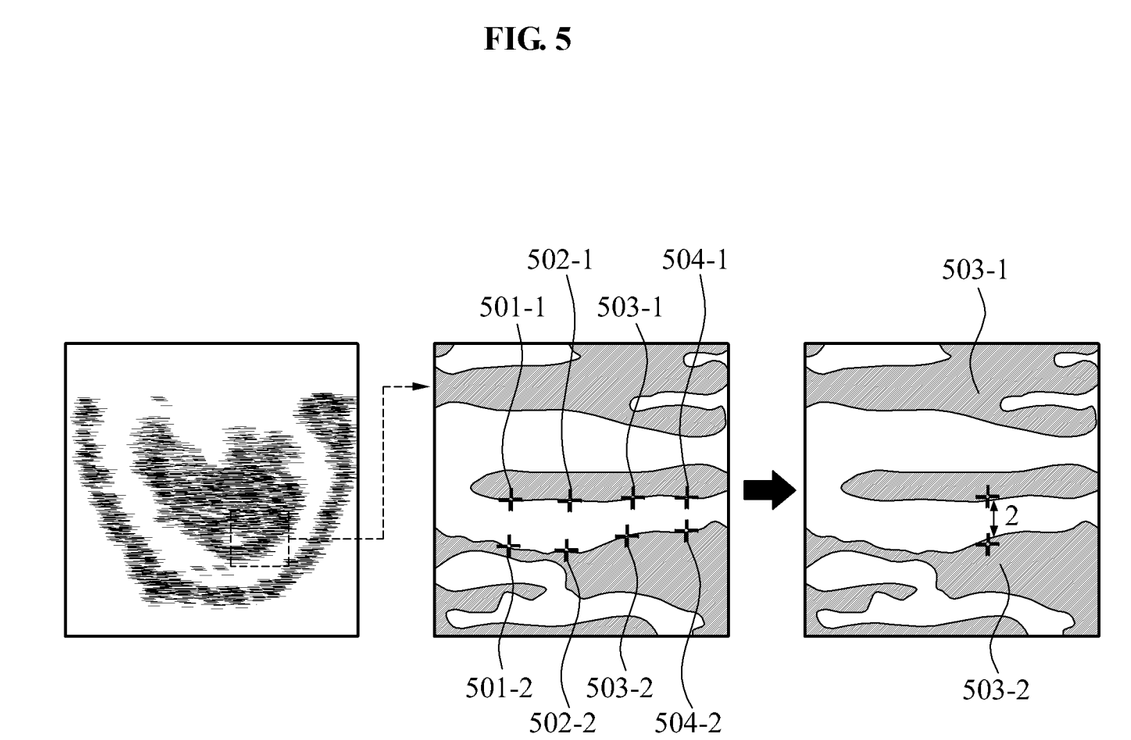
FIG. 5 is a view illustrating an example of measurement and display of a thickness of an image in the 3D ultrasound system according to another embodiment of the present invention.

FIG. 5 is a view illustrating an example for measurement and display of a thickness of an image in the 3D ultrasound system according to another embodiment of the present invention.

Referring to FIG. 5, the 3D ultrasound system may form an image with respect to an object in the body, may extract, from the image of the object, an image based on an inputted seed, for example, a surrounding image relative to the seed, and may display the extracted image.

For example, when the object is a fetus, the 3D ultrasound system may form an image of the fetus, may extract, from the image of the fetus, a surrounding image relative to a seed located near the NT of the fetus, and may display the surrounding image.

The 3D ultrasound system may locate a plurality of seeds on a horizontal line including the seeds, and may search for a gradient peak using each of the seeds. In this instance, the 3D ultrasound system may search for a first gradient peak and a second gradient peak of different locations for each of the plurality of seeds, and may measure a distance between the found first gradient peak and the found second gradient peak.

For example, when the extracted image is the NT of the fetus, the 3D ultrasound system may search for a first gradient peak_#1 '501_1' located in an upper area and a second gradient peak_#1 '501_2' located in a lower area, based on a first seed. Also, the 3D ultrasound system may search for a first gradient peak_#2 '502_1' located in an upper area and a second gradient peak_#2 '502_2' located in a lower area, based on a second seed. Similarly to the gradient peaks corresponding to the first and second seeds, the 3D ultrasound system may search for a first gradient peak_#3 '503_1' and a second gradient peak_#3 '503_2' corresponding to a third seed, and a first gradient peak_#4 '504_1' and a second gradient peak_#4 '504_2' corresponding to a fourth seed.

The 3D ultrasound system may measure a distance between the first gradient peak and the second gradient peak for each of the seeds, may calculate an average and a variation of the measured distances (for example, a first distance to a fourth distance), and may determine a maximum distance among distances of the image smaller than the sum of the average and the variation.

For example, when a distance between the first gradient peak_#3 '503_1' and the second gradient peak_#3 '503_2', that is, a third distance is determined based on the predetermined determination condition, the 3D ultrasound system may superimpose the third distance or the first gradient peak_#3 '503_1' and the second gradient peak_#3 '503_2' related to the third distance on the extracted image, and may display the resulting combination, thereby facilitating recognition of an area where the thickness of the NT of the fetus was measured.

Figure 6:
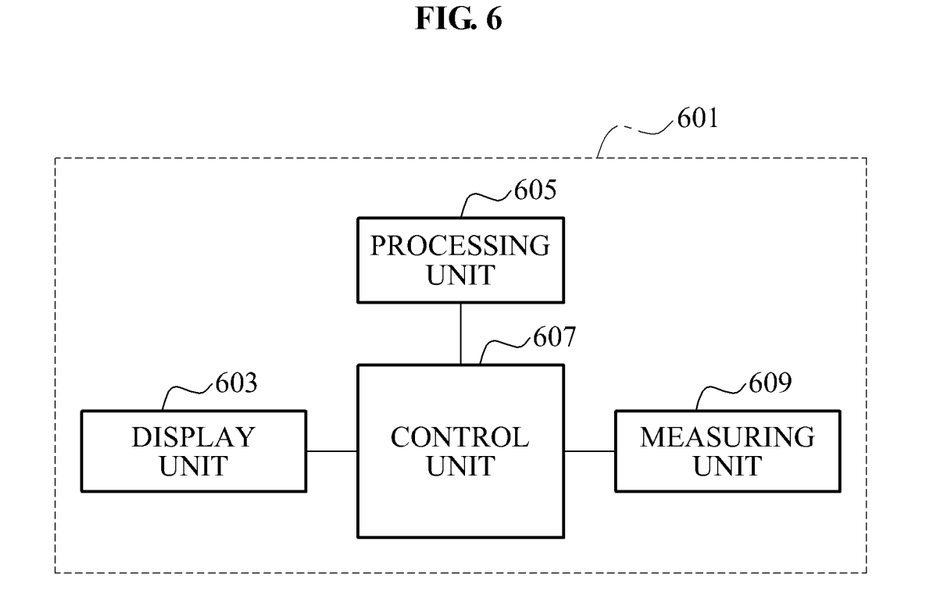
FIG. 6 is a block diagram illustrating a structure of a 3D ultrasound system according to still another embodiment of the present invention.

FIG. 6 is a block diagram illustrating a structure of a 3D ultrasound system 601 according to still another embodiment of the present invention.

Referring to FIG. 6, the 3D ultrasound system 601 according to still another embodiment of the present invention may include a display unit 603, a processing unit 605, a control unit 607, and a measuring unit 609.

The display unit 603 may form an image with respect to an object in the body, and may display the image on a screen. Here, the object in the body may be a fetus, a blood vessel, or an internal organ.

For example, the display unit 603 may set an ROI in the object, may locate a reference location, for example, a seed within the set ROI, and may form an image of the object by irradiating the object with an ultrasonic beam.

The processing unit 605 may perform a thresholding operation on the image based on predetermined brightness information. For example, the processing unit 605 may make the contour of the image clear by turning the image 'black' or 'white' depending on '0' and '1' given based on predetermined brightness information.

The control unit 607 may generate a figure template corresponding to the image, for example, in the shape of 'X' or '<', the figure template including a first straight line and a second straight line forming an angle, may adjust the generated figure template based on a reference location of the image, and may superimpose the adjusted figure template on the image and display the resulting combination.

In this instance, the control unit 607 may adjust the generated figure template based on location information inputted by an interface unit (not shown), for example, a point resulted from focusing on the image, or based on a central point of the object searched by a center extracting unit (not shown), as the reference location. Here, when the object is a fetus, the center extracting unit may generate a central point of the object using a first specific point related to the ridge of the nose of the fetus and a second specific point related to the jawbone of the fetus, and may provide the control unit 607 with the generated central point of the object as the reference location.

The control unit 607 may adjust the generated figure template by rotating, moving, or modifying the figure template based on the reference location of the image, and the modification may change an angle of the figure template. For example, the control unit 607 may elaborately adjust the generated figure template to be matched with the image, by changing locations of the first straight line and the second straight line of the figure template through rotation of the figure template, by matching a vertex corresponding to an angle of the figure template with the reference location through movement of the figure template, or by changing a size of an angle of the figure template.

For example, when the object is a fetus, the control unit 607 may adjust the figure template to locate the first straight line at the ridge of the nose of the fetus and by locating the second straight line at the jawbone of the fetus, the first straight line and the second straight line intersecting and forming an angle. In this instance, the vertex corresponding to the angle of the figure template may be located at, for example, a point where a connecting line of the reference location and the ridge of the nose of the fetus meets a connecting line of the reference location and the jawbone of the fetus.

In this instance, the control unit 607 may adjust the generated figure template with a minimum matching energy with the image. That is, the control unit 607 may adjust the generated figure template to be matched with the image at the maximum while reducing the matching energy by minimizing rotation, movement, or modification of the figure template.

When adjustment of the figure template is completed by the control unit 607, the measuring unit 609 may measure an angle of the figure template. In this instance, when the object is a fetus, the measuring unit 609 may measure an angle of the figure template located at the ridge of the nose and the jawbone of the fetus.

Also, the display unit 603 may display the angle of the figure template measured by the measuring unit 609, under the control of the control unit 607. In this instance, the display unit 603 may check the measured angle of the figure template and a predetermined angle range, and may further display a message about the check result.

For example, when the object is a fetus, the display unit 603 may display the angle of the figure template measured by the measuring unit 609 as a frontmaxillary facial (FMF) angle between the ridge of the nose of the fetus and the jawbone of the fetus. In this instance, the display unit 603 may match the measured angle of the figure template with an FMF angle range of a normal baby, and when the measured angle of the figure template is beyond the predetermined angle range, the display unit 609 may display a message about the check result, for example, 'possible Down syndrome'. Accordingly, an operator or a doctor may diagnose the condition of the fetus more accurately and more quickly.

Figure 7:
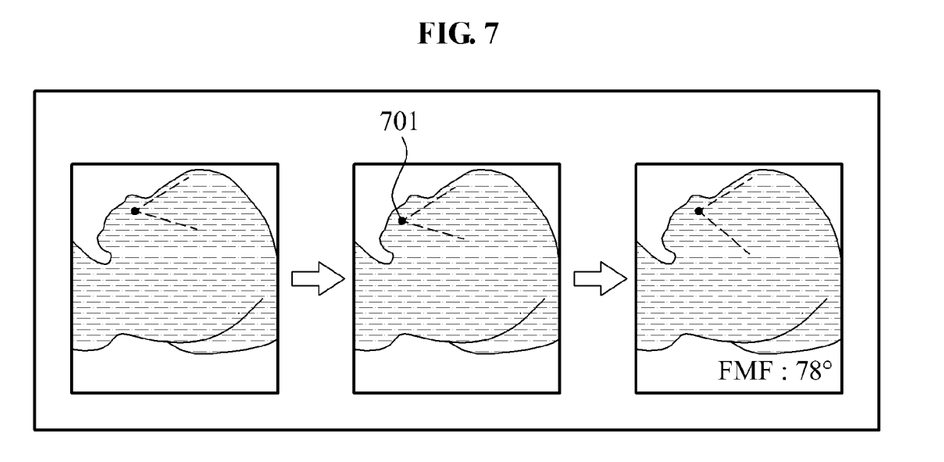
FIG. 7 is a view illustrating an example of adjustment of a figure template in the 3D ultrasound system according to still another embodiment of the present invention.

FIG. 7 is a view illustrating an example of adjustment of a figure template in the 3D ultrasound system according to still another embodiment of the present invention.

Referring to FIG. 7, the 3D ultrasound system may form an image with respect to an object in the body, and may display the image on a screen.

The 3D ultrasound system may generate a figure template corresponding to the image, including a first straight line and a second straight line forming an angle, may adjust the generated figure template based on a reference location of the image, and may superimpose the adjusted figure template on the image and display the resulting combination.

For example, when the object is a fetus, the 3D ultrasound system may generate a figure template corresponding to the image of the fetus in the shape of '<'. Subsequently, the 3D ultrasound system may move the figure template to locate a vertex corresponding to the angle of the figure template at a point 701 where a connecting line of the reference location and the ridge of the nose of the fetus meets a connecting line of the reference location and the jawbone of the fetus. In this instance, the 3D ultrasound system may adjust the figure template to locate the first straight line of the figure template at the ridge of the nose of the fetus.

Also, the 3D ultrasound system may adjust the figure template to locate the second straight line of the figure template at the jawbone of the fetus, by increasing or reducing the angle of the figure template.

When adjustment of the figure template is completed, the 3D ultrasound system may display the angle of the figure template together with the figure template. In this instance, when the angle of the figure template is 78° and an FMF angle range of a normal baby is, for example, between 75° and 80°, the 3D ultrasound system may further display 'no risk of Down syndrome' as a message about the check result because the angle of the figure template is within the predetermined angle range.

Figure 8:
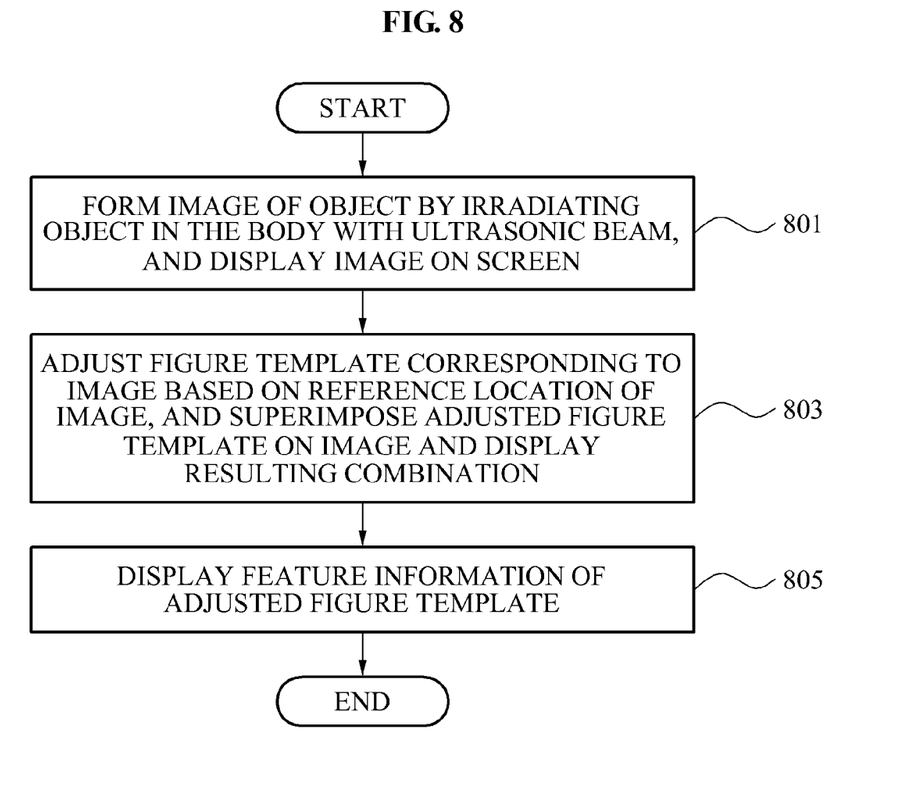
FIG. 8 is a flowchart illustrating a method for operating the 3D ultrasound system according to an embodiment of the present invention.

FIG. 8 is a flowchart illustrating a method for operating the 3D ultrasound system according to an embodiment of the present invention.

Referring to FIG. 8, the 3D ultrasound system may form an image with respect to an object in the body and may display the image on a screen, in operation 801.

In this instance, the 3D ultrasound system may set an ROI in the object, may locate a seed within the set ROI, and may form an image of the object by irradiating the object with an ultrasonic beam.

The 3D ultrasound system may perform a thresholding operation on the image based on predetermined brightness information. For example, the 3D ultrasound system may make the contour of the image clear by turning the image 'black' or 'white' depending on '0' and '1' given based on predetermined brightness information.

Also, the 3D ultrasound system may clearly distinguish an area to be measured in the image, by performing an edge detecting operation or an ellipse fitting operation on the image.

In operation 803, the 3D ultrasound system may generate a figure template corresponding to the image, for example, a circular or ellipse template, may adjust the generated figure template based on a reference location of the image, for example, a central point of the image, and may superimpose the adjusted figure template on the image and display the resulting combination.

In this instance, the 3D ultrasound system may adjust the generated figure template based on location information inputted by an interface unit (not shown), for example, a point resulted from focusing on the image, or based on a central point of the object measured by a center extracting unit (not shown), as the reference location.

Also, the 3D ultrasound system may adjust the generated figure template by rotating, moving, or modifying the figure template based on the reference location of the image, and the modification may change the BPD or OFD of the figure template. For example, the 3D ultrasound system may elaborately adjust the generated figure template to be matched with the image, by changing an angle of the figure template through rotation of the figure template, by changing a location of the figure template through movement of the figure template, or by changing a size of the figure template through a change in the BPD or OFD of the figure template.

The 3D ultrasound system may adjust the figure template to be matched with the image at the maximum while reducing the matching energy by minimizing rotation, movement, or modification of the figure template.

When adjustment of the figure template is completed, the 3D ultrasound system may display feature information of the adjusted figure template, in operation 805.

For example, the 3D ultrasound system may display at least one of BPD, OFD, HD and a ratio of BPD/OFD of the adjusted figure template.

According to an embodiment of the present invention, the 3D ultrasound system may generate a figure template corresponding to an image, may adjust the generated figure template to be matched with the image by rotating, moving, or modifying the figure template based on a reference location of the image, and may display feature information of the matched figure template, for example, BPD, OFD, HD, or a ratio of BPD/OFD, thereby automatically providing an accurate measurement result of the image.

Figure 9:
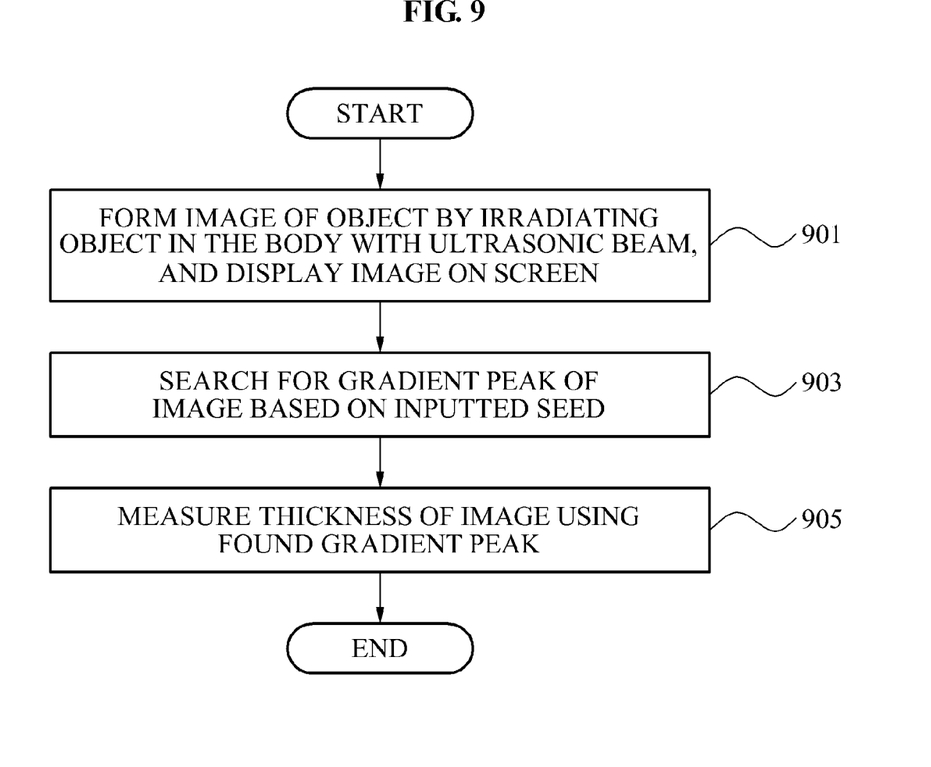
FIG. 9 is a flowchart illustrating a method for operating the 3D ultrasound system according to another embodiment of the present invention.

FIG. 9 is a flowchart illustrating a method for operating the 3D ultrasound system according to another embodiment of the present invention.

Referring to FIG. 9, the 3D ultrasound system may form an image with respect to an object in the body, and may display the image on a screen, in operation 901.

That is, the 3D ultrasound system may form an image with respect to an object in the body, may extract, from the image of the object, an image based on an inputted seed, for example, a surrounding image relative to the seed, and may display the extracted image. In this instance, when the object is a fetus, the seed may be located near the NT of the fetus.

The 3D ultrasound system may correct the extracted image as pre-processing for accurately measuring a thickness of the extracted image. For example, the 3D ultrasound system may make the contour of the extracted image clear by performing a thresholding operation or a multiplying operation on the image based on predetermined brightness information.

In operation 903, the 3D ultrasound system may search for a gradient peak of the image based on the inputted seed.

Specifically, the 3D ultrasound system may search for a zero-crossing on the extracted image based on the inputted seed, and may search for a gradient peak of the extracted image using the found zero-crossing. That is, the 3D ultrasound system may search for a first zero-crossing in an upper area and a second zero-crossing in a lower area based on the seed, and may search for a first gradient peak and a second gradient peak of the extracted image using the first zero-crossing and the second zero-crossing, respectively.

In this instance, the 3D ultrasound system may locate a plurality of seeds on a horizontal line including the seeds, and may search for a gradient peak using each of the seeds. Here, the 3D ultrasound system may search for a first gradient peak and a second gradient peak of different locations for each of the plurality of seeds.

In operation 905, the 3D ultrasound system may measure a thickness of the image using the found gradient peak.

In this instance, the 3D ultrasound system may measure a distance between the first gradient peak and the second gradient peak. For example, when the extracted image is the NT of a fetus, the 3D ultrasound system may search for a first gradient peak and a second gradient peak along the boundary of a transparent space located at the back of the neck of the fetus, and may measure a distance between the first gradient peak and the second gradient peak, thereby easily measuring a thickness of the NT of the fetus.

Also, when the first gradient peak and the second gradient peak for each of the plurality of seeds are found, the 3D ultrasound system may measure a distance between the first gradient peak and the second gradient peak, respectively. Subsequently, the 3D ultrasound system may determine one of a plurality of distances, that is, one of a plurality of thicknesses of the image and may display the determined one on a screen, thereby providing a more accurate thickness of the image.

For example, the 3D ultrasound system may calculate an average and a variation of the measured thicknesses of the image, may determine a maximum thickness among thicknesses of the image smaller than the sum of the average and the variation, and may superimpose a gradient peak corresponding to the determined thickness on the extracted image and display the resulting combination.

According to an embodiment of the present invention, the 3D ultrasound system may form an image, may search for a gradient peak of the image based on an inputted seed, and may automatically measure a thickness of the image using the found gradient peak, thereby easily providing an accurate measurement result of the thickness of the image.

According to an embodiment of the present invention, the 3D ultrasound system may generate a figure template corresponding to an image, may match the generated figure template with the image by adjusting the figure template based on a reference location of the image through rotation, movement, or modification, and may display feature information of the matched figure template, for example, BPD, OFD, HD, and a ratio of BPD/OFD, thereby automatically providing an accurate measurement result of the image.

Figure 10:
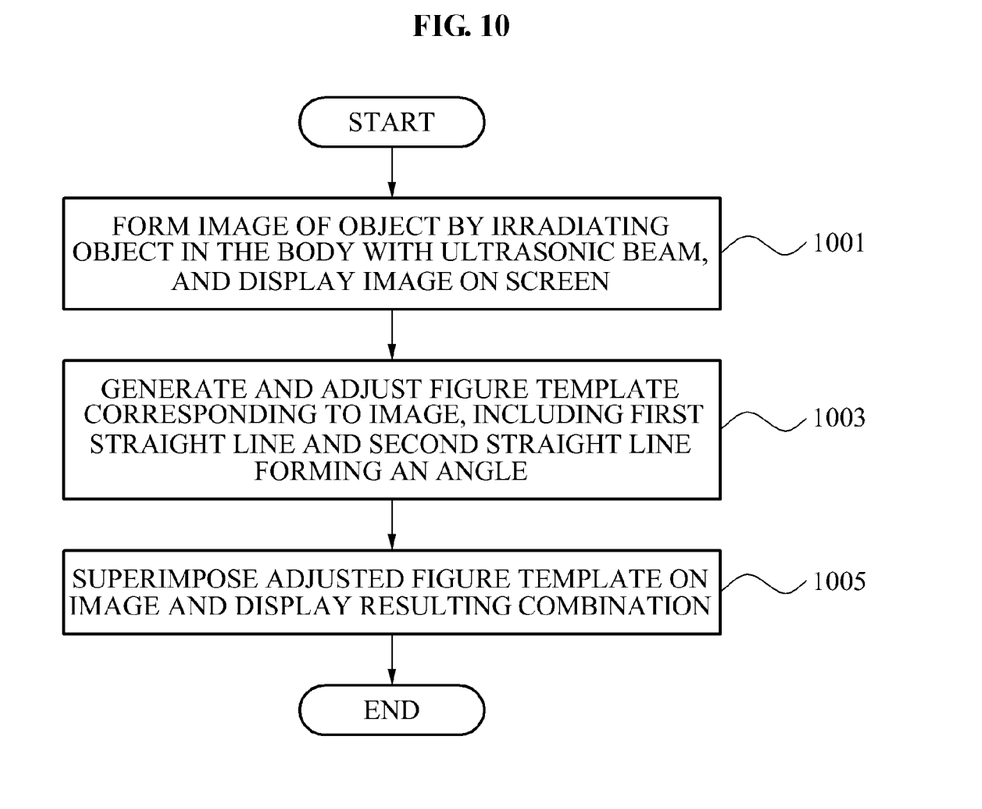
FIG. 10 is a flowchart illustrating a method for operating the 3D ultrasound system according to still another embodiment of the present invention.

FIG. 10 is a flowchart illustrating a method for operating the 3D ultrasound system according to still another embodiment of the present invention.

Referring to FIG. 10, the 3D ultrasound system may form an image with respect to an object in the body, and may display the image on a screen, in operation 1001.

In this instance, the 3D ultrasound system may set an ROI in the object, may locate a reference location, for example, a seed within the set ROI, and may form an image of the object by irradiating the object with an ultrasonic beam.

The 3D ultrasound system may perform a thresholding operation on the image based on predetermined brightness information. For example, the 3D ultrasound system may make the contour of the image clear by turning the image 'black' or 'white' depending on '0' and '1' given based on predetermined brightness information.

In operation 1003, the 3D ultrasound system may generate a figure template corresponding to the image, for example, in the shape of 'X' or '<', the figure template including a first straight line and a second straight line forming an angle, and may adjust the generated figure template based on a reference location of the image.

In this instance, the 3D ultrasound system may adjust the generated figure template based on location information inputted by an interface unit (not shown), for example, a point resulted from focusing on the image, or based on a central point of the object searched by a center extracting unit (not shown), as the reference location.

Also, the 3D ultrasound system may adjust the generated figure template by rotating, moving, or modifying the figure template based on the reference location of the image, and the modification may change an angle of the figure template. For example, the 3D ultrasound system may elaborately adjust the generated figure template to be matched with the image, by changing locations of the first straight line and the second straight line of the figure template through rotation of the figure template, by matching a vertex corresponding to an angle of the figure template with the reference location through movement of the figure template, or by changing a size of an angle of the figure template.

For example, when the object is a fetus, the 3D ultrasound system may adjust the figure template to locate the first straight line at the ridge of the nose of the fetus and to locate the second straight line at the jawbone of the fetus, the first straight line and the second straight line intersecting and forming an angle. In this instance, the vertex corresponding to the angle of the figure template may be located at, for example, a point where a connecting line of the reference location and the ridge of the nose of the fetus meets a connecting line of the reference location and the jawbone of the fetus.

In this instance, the 3D ultrasound system may adjust the generated figure template to be matched with the image at the maximum while reducing the matching energy by minimizing rotation, movement, or modification of the figure template.

When adjustment of the figure template is completed, the 3D ultrasound system may measure an angle of the figure template. In this instance, when the object is a fetus, the 3D ultrasound system may measure an angle of the figure template located at the ridge of the nose and the jawbone of the fetus.

In operation 1005, the 3D ultrasound system may superimpose the adjusted figure template on the image, and may display the resulting combination. In this instance, the 3D ultrasound system may check the measured angle of the figure template and a predetermined angle range, and may further display a message about the check result.

For example, when the object is a fetus, the 3D ultrasound system may display the measured angle of the figure template as an FMF angle between the ridge of the nose of the fetus and the jawbone of the fetus.

Also, the 3D ultrasound system may check the measured angle of the figure template and an FMF angle range of a normal baby, and when the measured angle of the figure template is beyond the predetermined angle range, the 3D ultrasound system may display a message about the check result, for example, 'possible Down syndrome'.

According to an embodiment of the present invention, the 3D ultrasound system may generate a figure template corresponding to an image of an object in the body, the figure template including a first straight line and a second straight line forming an angle, may adjust the generated figure template based on a reference location of the image, and may automatically measure and display an angle of the adjusted figure template, thereby providing an accurate measurement result of the angle of the image.

The above-described exemplary embodiments of the present invention may be recorded in non-transitory computer-readable media including program instructions to implement various operations embodied by a computer. The media may also include, alone or in combination with the program instructions, data files, data structures, and the like. Examples of non-transitory computer-readable media include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations of the above-described exemplary embodiments of the present invention, or vice versa.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. An ultrasound system comprising:
   a display configured to form an ultrasound image with respect to a fetus in a body and display the ultrasound image on a screen;
   a controller configured:
   to determine a reference position at a position where a first straight line corresponding to a ridge of a nose of the fetus and a second straight line corresponding to a jawbone of the fetus intersect,
   to generate a figure template comprising a vertex position at the reference position, the first straight line and the second straight line, wherein the first straight line and the second straight line form an angle,
   to automatically adjust the generated figure template so that a matching energy between the figure template and the ultrasonic image is reduced by changing the angle between the first straight line and the second straight line based on the vertex position, thereby measuring a front-maxillary facial (FMF) angle between the first straight line and the second straight line when the matching energy is minimized, to superimpose the adjusted figure template on the ultrasound image and display the resulting combination, and when the measured FMF angle is beyond a predetermined angle range, to automatically display an indication indicating a possibility that the fetus is in an abnormal condition.

2. The ultrasound system of claim 1, wherein the controller adjusts the generated figure template by rotating or moving the figure template based on the reference location of the ultrasound image, or by changing at least one of biparietal diameter (BPD), occipitofrontal diameter (OFD), and an angle of the figure template.

3. The ultrasound system of claim 1, wherein the controller is further configured to search for a zero-crossing on the ultrasound image based on an inputted seed and to search for a gradient peak of the ultrasound image using the zero-crossing, wherein the controller is further configured to measure a thickness of the ultrasound image using the gradient peak.

4. The ultrasound system of claim 3, wherein:

the controller is further configured to search for a first zero-crossing in an upper area and a second zero-crossing in a lower area based on the seed, and search for a first gradient peak and a second gradient peak of the ultrasound image using the first zero-crossing and the second zero-crossing, respectively, and the controller measures a distance between the first gradient peak and the second gradient peak.

5. The ultrasound system of claim 3, wherein:

the controller locates a plurality of seeds on a horizontal line including the seeds, and searches for a gradient peak using each of the seeds, and the controller measures a thickness of the ultrasound image using each of the gradient peaks, calculates an average and a variation of the measured thicknesses of the ultrasound image, and determines a maximum thickness among thicknesses of the ultrasound image smaller than the sum of the average and the variation.

6. The ultrasound system of claim 1, wherein the display configured to display the angle of the figure template measured by the controller as a frontmaxillary facial (FMF) angle between the ridge of the nose and the jawbone of the fetus.

7. A method for operating an ultrasound system, the method comprising:

forming an ultrasound image with respect to a fetus in the body and displaying the ultrasound image on a screen;

determining a reference position at a position where a first straight line corresponding to the ridge of a nose of the fetus and a second straight line corresponding to a jawbone of the fetus intersect;

generating a figure template comprising a vertex position at the reference position, the first straight line and the second straight line, wherein the first straight line and the second straight line form an angle;

automatically adjusting the generated figure template so that a matching energy between the figure template and the ultrasound image is reduced by changing the angle between the first straight line and the second straight line based on the vertex position, thereby measuring a front-maxillary facial (FMF) angle between the first straight line and the second straight line when the matching energy is minimized;

superimposing the adjusted figure template on the ultrasound image and displaying the resulting combination; and when the measured FMF angle is beyond a predetermined angle range, automatically displaying an indication indicating a possibility that the fetus is in an abnormal condition.

8. The method of claim 7, wherein the adjusting of the generated figure template comprises adjusting the generated figure template by rotating or moving the figure template based on a reference location of the ultrasound image, or by changing at least one of BPD, OFD, and an angle of the figure template.

9. The method of claim 7, further comprising:

searching for a zero-crossing on the ultrasound image based on an inputted seed and searching for a gradient peak of the ultrasound image using the zero-crossing; and measuring a thickness of the ultrasound image using the gradient peak.

10. The method of claim 9, wherein:

the searching of the gradient peak of the ultrasound image comprises searching for a first zero-crossing in an upper area and a second zero-crossing in a lower area based on the seed, and searching for a first gradient peak and a second gradient peak of the ultrasound image using the first zero-crossing and the second zero-crossing, respectively, and the measuring of the thickness of the ultrasound image comprises measuring a distance between the first gradient peak and the second gradient peak.

11. The method of claim 9, wherein:

the searching of the gradient peak of the ultrasound image comprises locating a plurality of seeds on a horizontal line including the seeds, and searching for a gradient peak using each of the seeds, and the measuring of the thickness of the ultrasound image comprises measuring a thickness of the ultrasound image using each of the gradient peaks, calculating an average and a variation of the measured thicknesses of the ultrasound image, and determining a maximum thickness among thicknesses of the ultrasound image smaller than the sum of the average and the variation.

* * * * *